US006844721B2

(12) United States Patent
Oliver

(10) Patent No.: US 6,844,721 B2
(45) Date of Patent: Jan. 18, 2005

(54) VARIABLE ELECTROMAGNETIC DAMPING APPARATUS

(75) Inventor: Warren C. Oliver, Knoxville, TN (US)

(73) Assignee: MTS Systems Corporation, Eden Prairie, MN (US)

(*) Notice: Subject to any disclaimer, the term of this patent is extended or adjusted under 35 U.S.C. 154(b) by 110 days.

(21) Appl. No.: 10/165,053

(22) Filed: Jun. 7, 2002

(65) Prior Publication Data

US 2003/0016007 A1 Jan. 23, 2003

Related U.S. Application Data

(60) Provisional application No. 60/296,676, filed on Jun. 7, 2001, and provisional application No. 60/209,550, filed on Jun. 7, 2001.

(51) Int. Cl.[7] .............................. G01B 7/14; G01B 7/30
(52) U.S. Cl. ............................ 324/207.17; 324/207.12
(58) Field of Search ....................... 324/207.11–207.26, 324/239, 228, 232, 233, 240–243, 262–263; 73/78, 81–83, 573, 578, 1.89

(56) References Cited

U.S. PATENT DOCUMENTS

| 2,226,847 A | * 12/1940 | Clark .......................... 338/31 |
| 4,127,889 A | 11/1978 | Asano et al. ................ 361/159 |
| 4,848,141 A | 7/1989 | Oliver et al. .................. 73/81 |

* cited by examiner

*Primary Examiner*—Jay Patidar
*Assistant Examiner*—Reena Aurora
(74) *Attorney, Agent, or Firm*—Westman, Champlin & Kelly, P.A.; S. Koehler

(57) ABSTRACT

The invention relates to a method and device for providing damping in a displacement device that moves an element. The displacement device has a permanent magnet generating a first magnetic field and a first coil movable with the element. The first coil receives a selected current from an external source to generate a second magnetic field. The damping method includes moving a second coil in at least one magnetic field to generate a current in the second coil. The method includes varying the current in the second coil to vary the damping in the displacement device.

36 Claims, 4 Drawing Sheets

VARIABLE ELECTROMAGNETIC DAMPING APPARATUS

CROSS-REFERENCE TO RELATED APPLICATIONS

This application claims the benefit of U.S. Provisional Application entitled "Electromagnetic Damping", Ser. No. 60/209,550, filed on Jun. 6, 2000 and claims benefit of 60/296,676 filed Jun. 7, 2001, both incorporated herein by reference.

BACKGROUND OF THE INVENTION

High resolution load controlled applications, such as an indentation system described in U.S. Pat. No. 4,848,141, can be adversely affected by environmental or internal noise sources that add excitation to the system. Increasing the damping of the system can be beneficial in mitigating the negative effects of noise on the system. However, there is a trade-off. Specifically, since the dynamic characteristics of the system are altered by increased damping, the ability to control the indentation system in a desired manner may be affected in some cases.

There is an ongoing need to address the problem of damping internal and external noise in high resolution load controlled devices without adversely affecting the dynamic characteristics of the system.

SUMMARY OF THE INVENTION

The invention relates to a method and device for providing damping in a displacement device that moves an element. The displacement device has a permanent magnet generating a first magnetic field and a first coil movable with the element. The first coil receives a selected current from an external source to generate a second magnetic field. The damping method includes moving a second coil in at least one magnetic field to generate a current in the second coil. The method includes varying the current in the second coil to vary the damping in the displacement device.

As another aspect, the displacement device described above can be embodied in a material testing machine used to test mechanical or physical properties of a test specimen, the movable element being adapted to engage (e.g. contact or support) the test specimen.

BRIEF DESCRIPTION OF THE ILLUSTRATIVE EMBODIMENTS

DETAILED DESCRIPTION OF THE ILLUSTRATIVE EMBODIMENTS

Electromagnetic damping operates on the principles of the Faraday's law and Lenz's law. Faraday's law provides that the electromotive force (Emf) induced in a circuit by a changing magnetic field is equal to the negative of the rate of change of the magnetic flux linking the circuit. Faraday's law is also known as the law of magnetic induction. Lenz's law is a consequence of Faraday's law and provides that whenever there is an induced Emf in a conductor, it is always in such a direction that the current it induces opposes the change, which caused the induced Emf. In other words, the induced current has a magnetic field, which opposes the original perturbation or change in magnetic flux.

In the particular case of a conductive object moving within a non-constant magnetic field, the movement of the object results in a change in the net magnetic flux incident upon the object. This change in magnetic flux generates a current in the object corresponding to the change in magnetic flux. The current in turn generates a corresponding magnetic field whose direction opposes the change in flux. Thus, any dynamic force applied to the object in the magnetic field produces a corresponding damping force acting to negate the effect of the exciting force. This effect serves to dampen excitation of the object.

Figure 1:
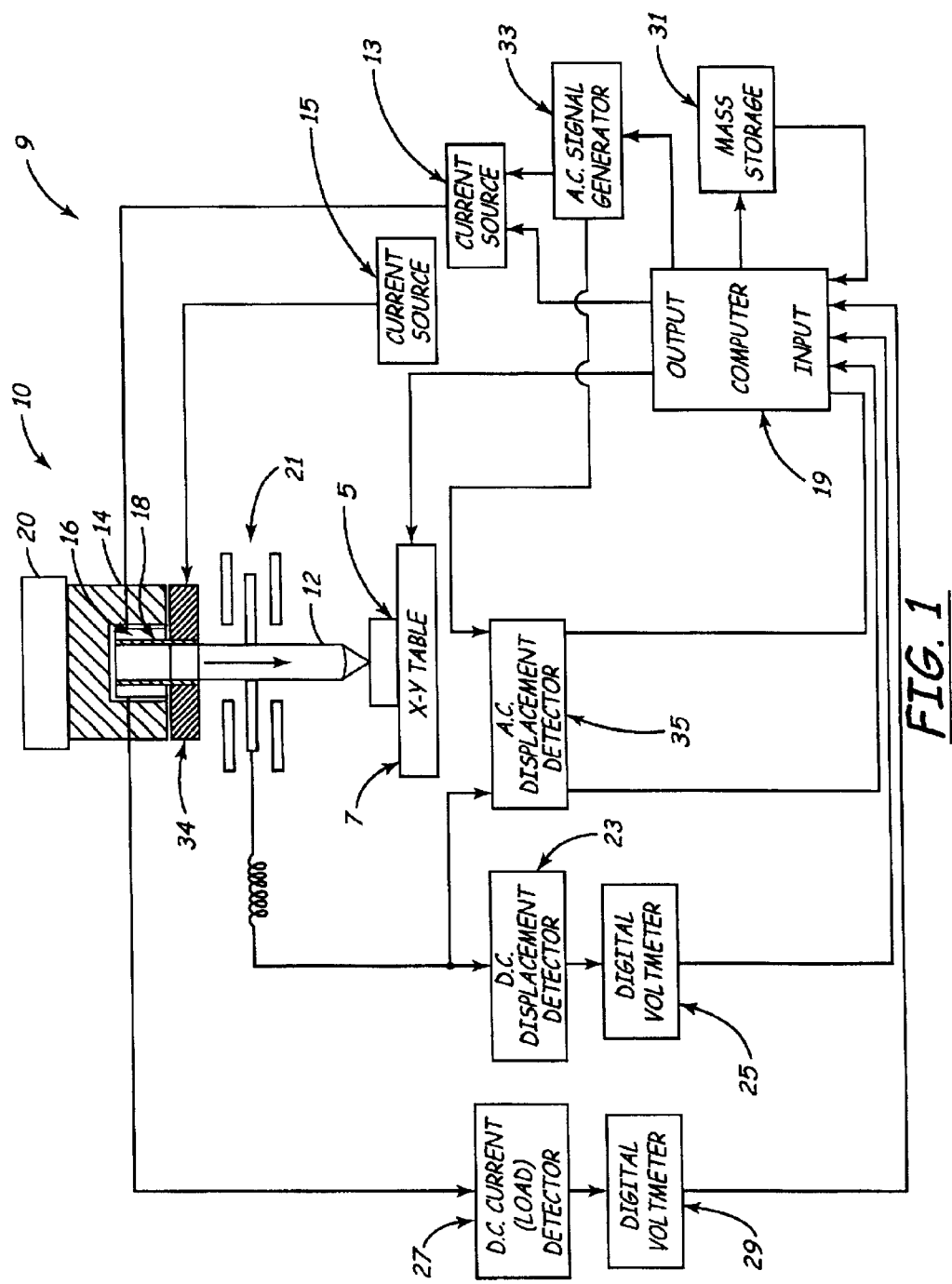
FIG. 1 is a schematic diagram of a commercially available indentation testing system with electromagnetic damping.

Generally illustrated in FIG. 1 is a system and method for providing damping in a displacement device 10 that moves an element 12, herein along a longitudinal axis thereof. The displacement device 10 can be an indenter as illustrated and described in U.S. Pat. No. 4,848,141, which is incorporated by reference in its entirety. Such systems are commercially available. For example, an indentation system sold under the trademark Nano Indenter® or the Dynamic Contact Module both made by MTS Systems Corporation of Eden Prairie, Minn. can be adapted to include the present invention. However, it should be understood that other types of displacement devices, and particularly material testing machines (such as the indenter and module referenced above) that are used to test mechanical or physical properties of test specimens, can benefit from the present invention.

Embodied as an indenter system 9, a sample of material 5 is placed at a known location on a computer controlled X-Y table 7 with the surface to be tested facing up. An electromagnetically driven indenter system 9 is provided which is positioned over the sample 5. The indenter system 9 includes a current drive or first coil 16 activated by the application of electrical current from a computer controlled variable current source 13 to move tip of element 12 downward into engagement with the sample 5. Once the tip contacts the sample a preselected force pattern is applied to the indenter by the programmed variation of the current applied to the first coil 16. Element 12 may have a tip of a typical triangular pyramidal diamond probe with an end radius of about 500 Angstroms.

The current source 13 is controlled by the system computer 19, which also controls the X-Y table 7. The displacement of element 12 is measured by a displacement gage 21, whose output is connected to a DC displacement detector 23. The detector 23 digitizes the DC displacement signal, which is fed through a digital voltmeter 25 to an input of the computer 19. The voltmeter 25 provides a calibrated readout of the probe displacement to an operator during testing procedures. Although illustrated as a capacitive displacement gage it should be understood other forms of gages can be used such as but not limited to gages that measure displacement using parameters of light (e.g. interferometers), resistivity, etc.

The force applied to the sample through element 12 is monitored by a DC current detector 27 which senses the DC drive current applied to the first coil 16. The DC load current is digitized by the detector 27 and fed through a second digital voltmeter 29 to a further input of computer 19. The computer may be connected to a mass storage device 31 in which data and system operating parameters are stored.

Using the system as described above, a sample 5 is positioned at a known location on the X-Y table 7 and the programmed computer 19 is signaled to start the test procedure. The computer is programmed to perform a prescribed indentation test, single or multiple indentations at designated locations on the sample, automatically. The probe is lowered at a very slow rate until contact is made with the sample. Then the computer applies a programmed increasing DC current from source 13 to the first coil 16 of the indenter which forces the indenter against the sample 5 until a preselected junction loading or displacement level is reached and then the force is removed at the same rate to unload the junction. During this loading and unloading cycle, the computer records the junction loading taken from the DC current (load) detector 27 and the probe displacement taken from the DC displacement detector 23. These values may be stored in the mass storage unit 31 for subsequent use in determining the various mechanical properties of the sample.

The system 9 can continuously measure the stiffness of the contact between two bodies such as the tip of element 12 and the sample 5 during the loading and unloading cycle. In particular, the system 9 includes a means for applying a small mechanical vibrational force to the junction of the indenter probe and the sample and monitoring the resulting displacement relative to the applied force as a measure of the stiffness between the two bodies. The force may be applied in the form of an oscillatory force (AC force), typically about $10^{-8}$ N (Newton), by superimposing an AC current onto the DC drive current applied to the drive coil 11. The frequency of the AC force applied is typically in the range of from 0.5 to 200 Hz for the system depicted in FIG. 1; however, depending on the design of the probe mounting assembly involved, the concept can work from about 0.5 Hz to 1 MHz. The amplitude of the oscillating force may be in the range of from about $10^{-10}$ to 1 N, depending on the area of the contact.

This procedure may be accomplished by adding an AC signal generator 33 under control of the computer 19 to inject an AC signal into the output current signal of the current source 17 and detecting the resulting AC displacement by means of an AC displacement detector 35. The detector 35 may be a lock-in amplifier, which is tuned to measure the amplitude of the AC displacement at the applied frequency together with the phase of the displacement signal relative to the applied signal. The amplitude and phase signals are digitized by the detector 35 and fed to separate inputs of the computer 19 for analysis or storage along with the DC force and displacement information during a loading and unloading cycle. Using the AC force (F), phase ($\Phi$) and AC displacement h ($\omega$) information, the stiffness (S) and other parameters of the test specimen may be determined as discussed in U.S. Pat. No. 4,848,141.

Figure 2:
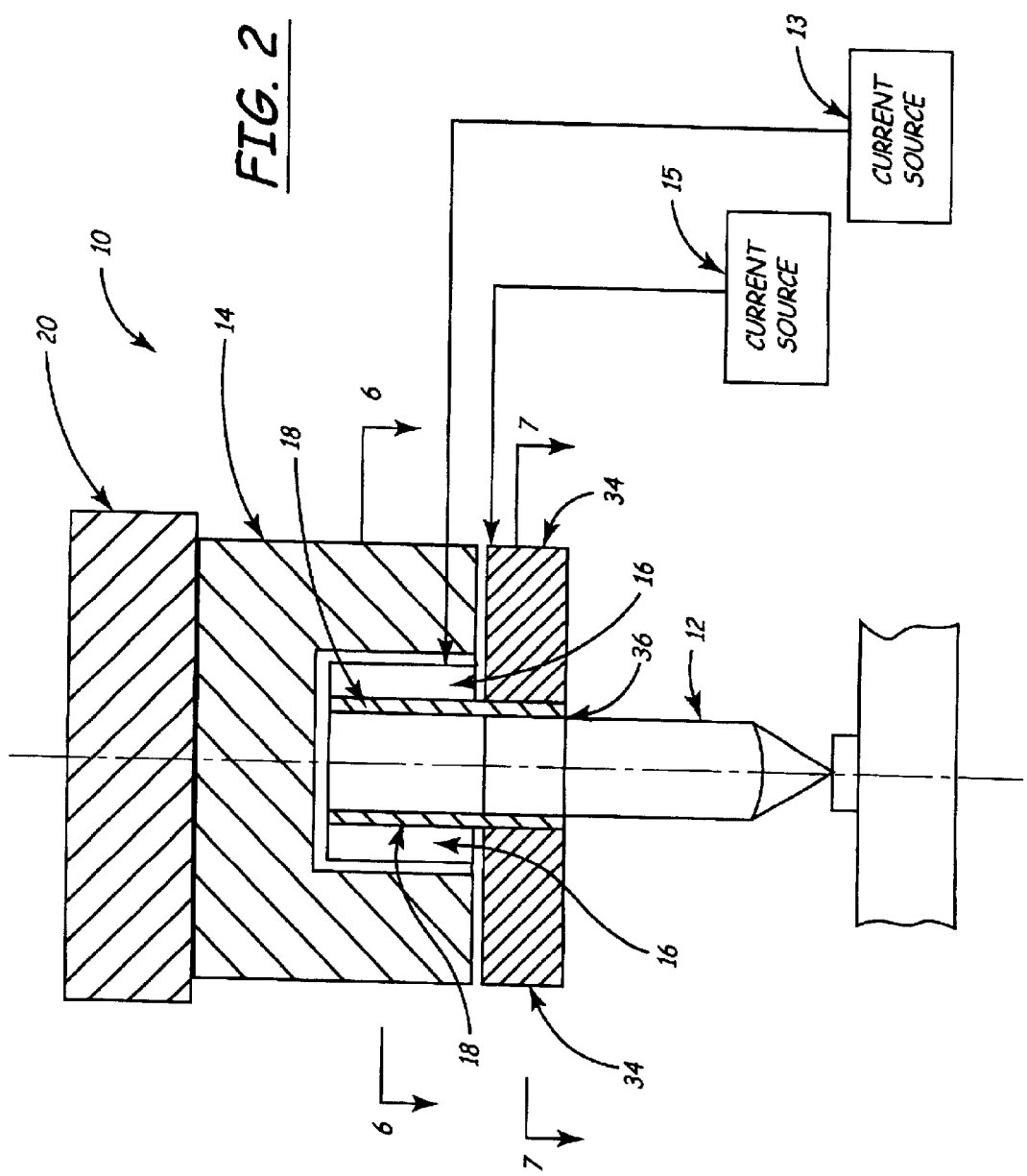
FIG. 2 is an enlarged sectional view of a displacement device with electromagnetic damping.

As schematically illustrated in FIGS. 1 and 2, displacement device 10 includes permanent magnet 14 generating a first magnetic field and first coil 16 movable with element 12. First coil 16 receives a current from external current source 13 to generate a second magnetic field. The system and method include moving a second coil 18 coupled to element 12 in a magnetic field to generate a current therein; and varying the current in the second coil 18 to vary the damping of displacement device 10. The means for adjusting damping movement of the movable element 12 includes varying the current in the second coil 18 to vary the damping of the displacement device 10.

One embodiment utilizes a method of varying the current in second coil 18 and is called a variable flux damper. In this embodiment, the means for adjusting damping movement of the movable element 12 includes changing the magnetic flux through which the second coil 18 moves. For instance, in the first embodiment, changing the magnetic flux includes repositioning permanent magnet 14 so as to change the amount of magnetic flux experienced by second coil 18. Positioner 20 coupled to permanent magnet 14 displaces permanent magnet 14 in order to change the magnetic flux. Positioner 20 can move permanent magnet 14 in any direction to change the magnetic flux. For example, positioner 20 can move permanent magnet 14 up or down, along the longitudinal axis of displacement of movable element 12. Likewise, positioner 20 can move permanent magnet 14 obtusely with respect to the longitudinal axis as well as perpendicular to the longitudinal axis. It should be noted that just a portion of permanent magnet 14 can be repositioned, if desired. Positioner 20 can be manually or computer-controlled.

Positioner 20 can take many forms. For example, positioner 20 can be a mechanical device with gears or other suitable drive elements to perform movements. In another embodiment, positioner 20 can be a simple actuator, such as a hydraulic actuator, a pneumatic actuator, a linear motor, or a drive screw. As used herein, means for adjusting damping movement of movable element 12 also includes merely removing a portion of permanent magnet 14, or replacing permanent magnet 14 with one of greater or lesser strength. Each of these techniques also varies the current induced in second coil 18. It should be noted that the orientation of components illustrated in FIGS. 1 and 2, such as positioner 20, magnet 14 and coil 18 can take many forms. The schematic illustration of FIGS. 1 and 2 are not intended to be limiting.

Figure 3:
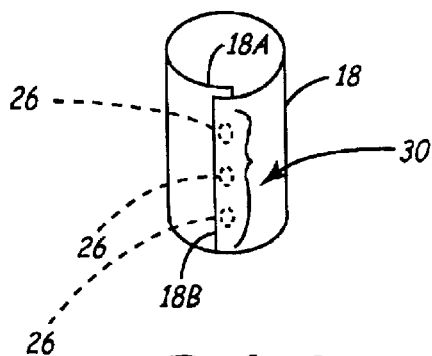
FIG. 3 is a schematic diagram of a coil having variable resistance.
Figure 6:
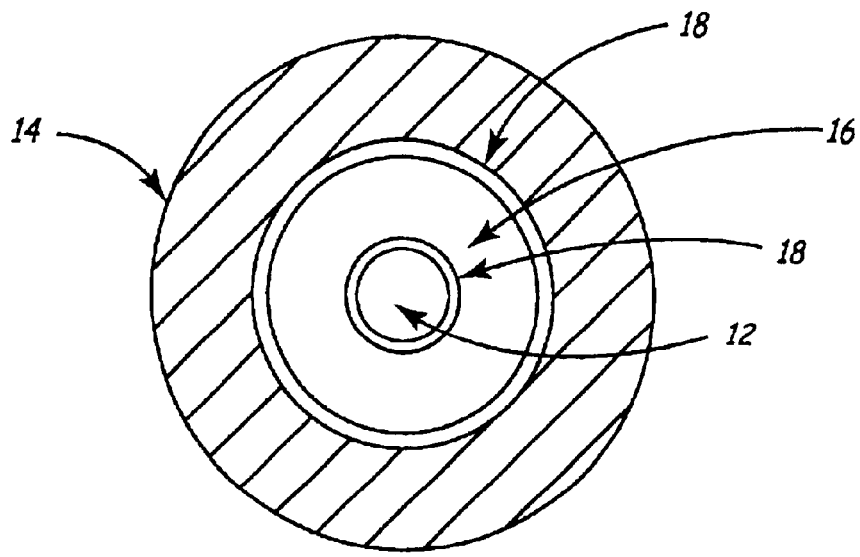
FIG. 6 is a section taken along line 6—6 of FIG. 2 and illustrates alternate positions of a damping coil.

In another embodiment, the resistance of the second coil 18 is adjusted in order to vary the current therein to adjust the damping movement of the movable element 12, and herein is called a resistance damper. Lower resistance in second coil 18 is associated with higher induced current and thus greater damping. Conversely, higher resistance is associated with lower induced current and less damping. Referring to FIG. 3, second coil 18 commonly comprises a single turn cylindrical sleeve of conductive material that is secured to the movable element 12, for example, concentrically underneath or over the first coil 16, which receives drive current from external current source 13 (shown on FIGS. 1 and 2). FIG. 6 is a section taken along line 6—6 of FIG. 2 and illustrates alternate positions for second coil 18 underneath or over first coil 16. Second coil 18 is electrically insulated from first coil 16.

Various techniques can be used to adjust the resistance of second coil 18 in order to adjust the damping of movable element 12. In a first technique, the size or configuration of the second coil 18 can be varied in order to change its resistance. For instance, various sizes (e.g. different diameters) of coils can be available, wherein the coils are installed selectively to vary the resistance of second coil 18.

Figure 4:
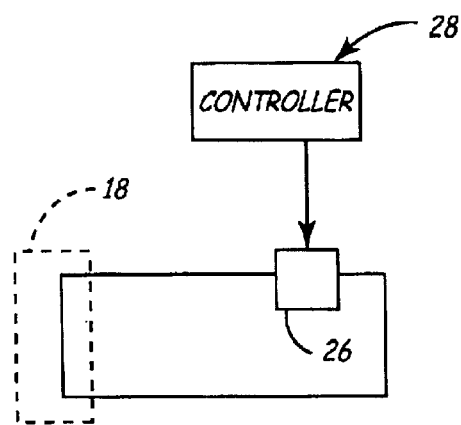
FIG. 4 is a schematic diagram of a system for varying resistance in a damping coil.

FIG. 4 schematically illustrates another technique wherein an electronic switch 26 completes a conductive path of second coil 18. Generally, electronic switch 26 is switchable from a relatively low resistant state to a relatively high resistant state. In a further embodiment, the operating point of electronic switch 26 is controlled in a range between a relatively low resistant state and a relatively high resistant state. Transistors of various forms can operate in this manner.

Electronic switch 26 can be external to second coil 18. However, in view of the low resistance of second coil 18, it may be preferable to locate electronic switch 26 as close to second coil 18 as possible in order to minimize the resistance between electronic switch 26 and second coil 18.

Figure 5:
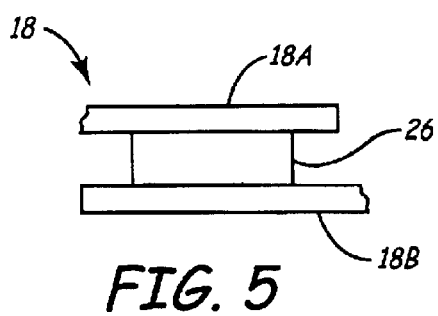
FIG. 5 is a schematic diagram of an electronic switch disposed between overlapping portions of a damping coil.

FIGS. 3 and 5 illustrate one embodiment wherein at least one electronic switch 26 is disposed between overlapping portions 18A and 18B of second coil 18. It should be noted that FIG. 5 is schematic in that dimensions of elements disposed therein have been exaggerated for purposes of understanding. In FIG. 4, command signals are provided from controller 28 to electronic switch 26. The length of the conductors used for the command signals is chosen for convenience, since the resistance of the signal path of the command signals does not affect the overall resistance of second coil 18. It should be noted that electronic switches that operate using light as a command signal can also be used. Similarly, other forms of electronic switches well known in the art can also be used.

In a further embodiment, a plurality 30 of electronic switches 26 connected in parallel, such as illustrated in FIG. 3, can be used to complete the conductive path of second coil 18. Each of the electronic switches 26 can be operated separately, if desired, wherein each electronic switch 26 includes a relatively low resistant state and a relatively high resistant state. Likewise, each electronic switch 26 can be adjusted to have an operating point within a range from the relatively low resistant state to the relatively high resistant state.

Figure 7:
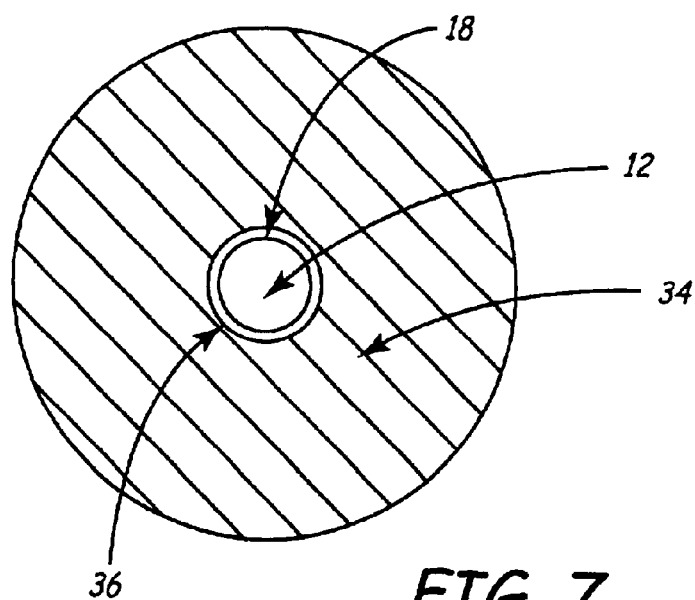
FIG. 7 is a section taken along line 7—7 of FIG. 2.

Another embodiment of adjusting damping is also illustrated in FIGS. 1, 2 and 7. FIG. 7 is a section taken along line 7—7 of FIG. 2. In this embodiment, third coil 34 is provided having aperture 36 for receiving movable element 12 and second coil 18 Third coil 34 receives a current from external current source 15 to induces a third magnetic field, wherein the movement of the second coil 18 in the third magnetic field generates a current to provide damping. As illustrated, third coil 34 can be spaced apart from permanent magnet 14 along an axis of movement of the movable element 12. In this manner, the amount of damping can be adjusted from zero to a maximum level since second coil 18 moves in the third magnetic field. In other words, the second coil 18 can be positioned on element 12 so as to interact with only the magnetic field of third coil 34. In another embodiment, the second coil can be positioned on the element 12 so as to interact with the magnetic fields of magnet 14 and third coil 34. The third magnetic field can be adjustable by adjusting the current provided to third coil 34 from external current source 15.

As appreciated by those skilled in the art, features of the embodiments described above can be combined, if desired.

Although the present invention has been described with reference to preferred embodiments, workers skilled in the art will recognize that changes may be made in form and detail without departing from the spirit and scope of the invention.

What is claimed is:

1. A method for providing damping in a displacement device that moves an element, the displacement device having a permanent magnet generating a first magnetic field and a first coil movable with the element, the first coil receiving an external current to generate a second magnetic field, the method comprising:
   moving a second coil in at least one magnetic field; and
   varying the current in the second coil to vary the damping in the displacement device.

2. The method of claim 1 wherein moving the second coil includes moving the second coil in the first magnetic field, and wherein varying the current in the second coil comprises adjusting a position of the permanent magnet relative to the second coil.

3. The method of claim 1 wherein moving the second coil includes moving the second coil in the first magnetic field, and wherein varying the current comprises varying the resistance of the second coil.

4. The method of claim 3 wherein varying the resistance comprises operating an electronic switch that completes a conductive path of the second coil.

5. The method of claim 4 wherein operating the electronic switch comprises selectively switching the switch from a relatively low resistance state to a relatively high resistance state.

6. The method of claim 4 wherein operating the electronic switch comprises selectively controlling an operating point of the switch to be at a position in a range between a relatively low resistance state and a relatively high resistance state.

7. The method of claim 3 wherein varying the resistance comprises selectively operating a plurality of electronic switches that complete a plurality of conductive paths of the second coil.

8. The method of claim 7 wherein operating the plurality of electronic switches comprises selectively switching each of the switches from a relatively low resistance state to a relatively high resistance state.

9. The method of claim 7 wherein operating the plurality of electronic switches comprises selectively controlling an operating point of each of the switches to be at a position in a range between a relatively low resistance state and a relatively high resistance state.

10. The method of claim 1 wherein varying the current comprises generating a third magnetic field, and wherein moving the second coil comprises moving the second coil in the third magnetic field.

11. A displacement device comprising:
   a permanent magnet generating a first magnetic field;
   a movable element;
   a first coil secured to the movable element, the coil receiving current to generate a second magnetic field;
   a second coil to move with the movable element; and
   means for adjusting damping movement of the movable element, wherein the means for adjusting damping comprises means for adjusting a resistance of the second coil.

12. The displacement device of claim 11 wherein the second coil comprises a single turn cylindrical sleeve of conductive material.

13. The displacement device of claim 11 wherein the second coil is movable in the first magnetic field and the means for adjusting comprises an electronic switch that completes a conductive path of the second coil.

14. The displacement device of claim 13 wherein the electronic switch is switchable from a relatively low resistance state to a relatively high resistance state.

15. The displacement device of claim 13 wherein an operating point of the switch can be controlled in a range between a relatively low resistance state and a relatively high resistance state.

16. The displacement device of claim 11 wherein the means for adjusting the resistance comprises a plurality of electronic switches, each switch selectively completing a conductive path of the second coil.

17. The displacement device of claim 16 wherein each of the switches is switchable from a relatively low resistance state to a relatively high resistance state.

18. The displacement device of claim 16 wherein an operating point of each of the switches can be controlled in a range between a relatively low resistance state and a relatively high resistance state.

19. A displacement device comprising:
a permanent magnet generating a first magnetic field;
a movable element;
a first coil secured to the movable element, the coil receiving current to generate a second magnetic field;
a second coil to move with the movable element; and
means for adjusting damping movement of the movable element, wherein the means for adjusting damping comprises a third coil having an aperture receiving the movable element and the second coil, the third coil selectively receiving an external current to generate a third magnetic field, wherein the movement of the second coil in the third magnetic coil provides damping to the element.

20. The displacement device of claim 19 wherein the third coil is spaced apart from the permanent magnet along an axis of movement of the movable element.

21. A displacement device comprising:
a permanent magnet generating a first magnetic field;
a movable element;
a first coil secured to the movable element, the coil receiving current to generate a second magnetic field;
a second coil to move with the movable element; and
means for adjusting damping movement of the movable element, wherein the means for adjusting damping comprises a positioner coupled to the permanent magnet, and wherein the second coil moves in the first magnetic field.

22. A displacement device comprising:
a permanent magnet generating a first magnetic field;
a movable element;
a first coil secured to the movable element, the coil receiving current to generate a second magnetic field;
a second coil secured to the element to move with the element in the first magnetic field; and
an electronic switch that selectively completes a conductive path of the second coil.

23. The displacement device of claim 22 and further comprising a plurality of electronic switches, each switch selectively completing a conductive path of the second coil.

24. The displacement device of claim 23 wherein the second coil comprises a single turn coil.

25. The displacement device of claim 24 wherein the second coil comprises a cylindrical sleeve of conductive material.

26. A material testing machine for testing mechanical properties of a test specimen, the material testing machine comprising:
a permanent magnet generating a first magnetic field;
a movable element adapted to engage a test specimen;
a first coil secured to the movable element, the coil receiving current to generate a second magnetic field;
a second coil to move with the movable element; and
means for adjusting damping movement of the movable element, wherein the means for adjusting damping comprises means for adjusting a resistance of the second coil.

27. The material testing machine of claim 26 wherein the second coil comprises a single turn cylindrical sleeve of conductive material.

28. The material testing machine of claim 26 wherein the second coil is movable in the first magnetic field and the means for adjusting comprises an electronic switch that completes a conductive path of the second coil.

29. The material testing machine of claim 28 wherein the electronic switch is switchable from a relatively low resistance state to a relatively high resistance state.

30. The material testing machine of claim 28 wherein an operating point of the switch can be controlled in a range between a relatively low resistance state and a relatively high resistance state.

31. The material testing machine of claim 26 wherein the means for adjusting the resistance comprises a plurality of electronic switches, each switch selectively completing a conductive path of the second coil.

32. The material testing machine of claim 31 wherein each of the switches is switchable from a relatively low resistance state to a relatively high resistance state.

33. The material testing machine of claim 31 wherein an operating point of each of the switches can be controlled in a range between a relatively low resistance state and a relatively high resistance state.

34. A material testing machine for testing mechanical properties of a test specimen, the material testing machine comprising:
a permanent magnet generating a first magnetic field;
a movable element adapted to engage a test specimen;
a first coil secured to the movable element, the coil receiving current to generate a second magnetic field;
a second coil to move with the movable element; and
means for adjusting damping movement of the movable element, wherein the means for adjusting damping comprises a third coil having an aperture receiving the movable element and the second coil, the third coil selectively receiving an external current to generate a third magnetic field, wherein the movement of the second coil in the third magnetic coil provides damping to the element.

35. The material testing machine of claim 34 wherein the third coil is spaced apart from the permanent magnet along an axis of movement of the movable element.

36. A material testing machine for testing mechanical properties of a test specimen, the material testing machine comprising:
a permanent magnet generating a first magnetic field;
a movable element adapted to engage a test specimen;
a first coil secured to the movable element, the coil receiving current to generate a second magnetic field;
a second coil to move with the movable element; and
means for adjusting damping movement of the movable element, wherein the means for adjusting damping comprises a positioner coupled to the permanent magnet, and wherein the second coil moves in the first magnetic field.

* * * * *